United States Patent
Higgins et al.

(10) Patent No.: US 9,802,001 B2
(45) Date of Patent: Oct. 31, 2017

(54) DISPENSING SPEED CONTROL MECHANISM AND INJECTION DEVICE

(71) Applicant: SANOFI, Paris (FR)

(72) Inventors: Daniel David Higgins, Bristol (GB); Matthew Jones, Warwick (GB); Joseph Butler, Rugby (GB); William Marsh, Buckingham (GB)

(73) Assignee: Sanofi, Paris (FR)

( * ) Notice: Subject to any disclaimer, the term of this patent is extended or adjusted under 35 U.S.C. 154(b) by 232 days.

(21) Appl. No.: 14/782,745

(22) PCT Filed: Apr. 8, 2014

(86) PCT No.: PCT/EP2014/057000
§ 371 (c)(1),
(2) Date: Oct. 6, 2015

(87) PCT Pub. No.: WO2014/166918
PCT Pub. Date: Oct. 16, 2014

(65) Prior Publication Data
US 2016/0067420 A1 Mar. 10, 2016

(30) Foreign Application Priority Data
Apr. 10, 2013 (EP) .................................... 13163108

(51) Int. Cl.
*A61M 5/315* (2006.01)
*A61M 5/20* (2006.01)
*A61M 5/24* (2006.01)

(52) U.S. Cl.
CPC .......... *A61M 5/31551* (2013.01); *A61M 5/20* (2013.01); *A61M 5/31525* (2013.01);
(Continued)

(58) Field of Classification Search
CPC .......... A61M 5/31551; A61M 5/31583; A61M 5/31553; A61M 2005/2086
See application file for complete search history.

(56) References Cited

U.S. PATENT DOCUMENTS

| 4,333,459 A | 6/1982 | Becker |
| 4,902,279 A | 2/1990 | Schmidtz et al. |
| 2011/0077595 A1 | 3/2011 | Eich et al. |

FOREIGN PATENT DOCUMENTS

| EP | 0 956 875 | 11/1999 |
| EP | 2 198 903 | 6/2010 |

(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.

(Continued)

*Primary Examiner* — Bradley Osinski
(74) *Attorney, Agent, or Firm* — Fish & Richardson P.C.

(57) ABSTRACT

The present invention relates to a dispensing speed control mechanism for use in an injection device. The injection device may have a housing (10, 30, 40; 40'; 40"; 40''') and a drive member (70), which is driven by a power reservoir (100, 100') and axially movable between a dose setting position, in which the drive member (70) is rotationally constrained to the housing (10, 30, 40; 40'; 40"; 40'''), and a dose dispensing position, in which the drive member (70) is rotationally de-coupled from the housing (10, 30, 40; 40'; 40"; 40'''). The speed control mechanism comprises friction means (42) for retarding the drive member (70) during dose dispensing depending on the axial position of the drive member (70). Further, the invention relates to an injection device with such a dispensing speed control mechanism.

15 Claims, 6 Drawing Sheets

Figure 1:
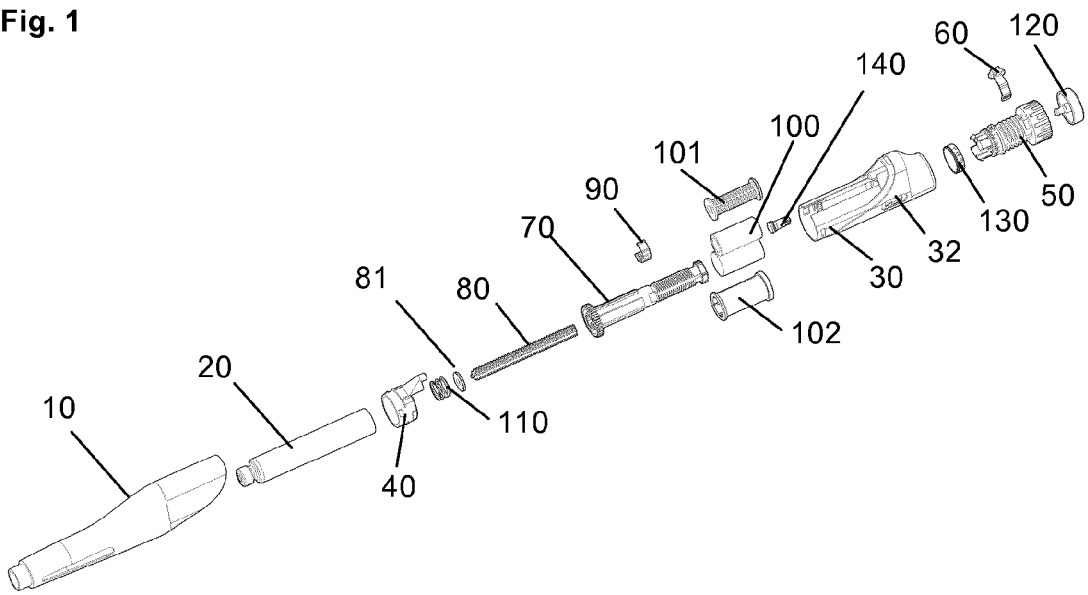

(52) U.S. Cl.
CPC .... *A61M 5/31553* (2013.01); *A61M 5/31583* (2013.01); *A61M 5/31591* (2013.01); *A61M 5/24* (2013.01); *A61M 5/31558* (2013.01); *A61M 5/31561* (2013.01); *A61M 2005/2086* (2013.01)

(56) References Cited

FOREIGN PATENT DOCUMENTS

| | | |
|---|---|---|
| WO | WO 2004/078241 | 9/2004 |
| WO | WO 2008/053243 | 5/2008 |

OTHER PUBLICATIONS

International Preliminary Report on Patentability in International Application No. PCT/EP2014/057000, dated Oct. 13, 2015, 5 pages.
International Search Report and Written Opinion in International Application No. PCT/EP2014/057000, dated Jul. 22, 2014, 7 pages.

DISPENSING SPEED CONTROL MECHANISM AND INJECTION DEVICE

CROSS-REFERENCE TO REATED APPLICATIONS

This application is a 371 U.S. National Phase Application of International Application Serial No. PCT/EP2014/057000, filed on Apr. 8, 2014, entitled "DISPENSING SPEED CONTROL MECHANISM AND INJECTION DEVICE" which claims priority to European Application Serial No. 13163108.7, filed on Apr. 10, 2013 the entire contents of which are hereby incorporated by reference.

The present invention is generally directed to a handheld injection device, i.e. a drug delivery device for selecting and dispensing a number of user variable doses of a medicament. In more detail, the invention refers to a dispensing speed control mechanism and an injection device with such a speed control mechanism.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is in general applicable for both types of devices, i.e. for disposable devices as well as for reusable devices.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A disposable drug delivery device for selecting and dispensing a number of user variable doses of a medicament according to the present invention typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. This known device is a manually driven device, where the component parts are in general disposed concentrically around a common longitudinal axis. During dose setting some component parts wind out of the housing and are pushed back into the housing during dose dispensing.

In the following, the distal end of an injection device or drive mechanism is referred to as the end where a cartridge and e.g. a needle are located, whereas the opposite end is the proximal end. A dose button may be provided at the proximal end.

A further differentiation of drug delivery device types refers to the drive mechanism: There are devices which are manually driven, e.g. by a user applying a force to an injection button like in WO 2004/078241 A1, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

EP 2 198 903 A1 discloses a motor mechanism for a drug delivery device with a spring in the form of a strip of spring metal sheet attached to two drums.

Manually driven devices have the advantage, that a user is able to control the speed of dose dispensing by individually adapting the pressure exerted e.g. to a button or trigger during dose dispensing. In contrast to that spring-type devices typically have the dispensing speed determined by the spring forces without giving the user the possibility to control or amend the speed.

EP 0 956 875 A2 discloses an injection device with an element which is pushed in the distal direction by a compression spring to advance a cartridge with a needle. For compensation of the varying spring force, a ring is provided causing friction between this element and a further element, wherein due to the geometry of the elements the friction decreases as the cartridge is pushed forward.

Further, U.S. Pat. Nos. 4,902,279 and 4,333,459 use friction in injection devices to control the axial movement of components.

A drug delivery device with a spring for axially displacing a drive rod is known from WO 2008/053243 A2. A trigger is provided on a lateral side of the device. In order to control the rate of ejection, the trigger may be pressed harder, which pushes a trigger brake against a plate, which in turn presses against a drum cylinder. By varying the amount of force used to press the trigger, the user varies the amount of friction force acting on the drum cylinder and, hence, controls the speed of movement of the drum cylinder. One potential drawback of this design is that the trigger brake is located on the lateral side of the device, which may make it difficult to use the trigger brake for patients with impaired dexterity.

It is an object of the present invention to provide an improved dispensing speed control mechanism and a spring-type drug delivery device allowing a user to control the speed of dose dispensing. It is a further object to improve user friendliness and handling and to make the drug delivery device compact in size, preferably without components translating out of the housing during dose setting.

This object is solved by a mechanism with the features of claim 1. According to a first embodiment of the present invention, the dispensing speed control mechanism is suitable for use in an injection device, which comprises a housing and a drive member, which is driven by a power reservoir, for example a spring, and is axially movable between a dose setting position, in which the drive member is rotationally constrained to the housing, and a dose dispensing position, in which the drive member is rotationally de-coupled from the housing. The drive member may have a range of dose dispensing positions. The speed control mechanism comprises friction means for retarding rotation of the drive member during dose dispensing depending on the axial position of the drive member. In other words, the user is able to control the dispensing speed by increasing or decreasing friction within the device and thus use either the full dispensing speed provided by the power reservoir or a speed reduced due to the internal friction. As the drive member is axially movable between a dose setting position, preferably a proximal position, in which the drive member is rotationally constrained to the housing, and a dose dispensing position, preferably a distal position, in which the drive member is rotationally de-coupled from the housing, irrespective of for example a spring load acting on the drive member, the drive member is prevented from rotation in its dose setting position.

Preferably, the drive member has to be axially displaced a first distance to initiate dose dispensing, e.g. by actuating a release button releasing a clutch, and may then be further axially displaced a second distance to control and amend dispensing speed. This may include examples where due to the position of the drive member there is either friction retarding the drive member or not. As an alternative, the magnitude of the friction retarding the drive member may be individually and preferably steplessly amended or adjusted by varying the position of the drive member.

In a preferred embodiment, the friction is at a high level just after the drive member is decoupled from the housing, i.e. displaced the first distance, and decreases as the drive member is further displaced for the full or fractions of the second distance. Typically, the drive member is pressed in an axial direction of the housing and relative to the housing.

In general, there are different ways to create the friction decelerating the drive member. For example a component part may be pressed against the drive member. As an alternative, a ratchet may be provided which may be brought into and out of engagement with the drive member. Further, a flexible element may be used which acts on the drive member. According to a preferred embodiment the friction means comprises a clicker mechanism with a clicker arm, which is rotationally constrained to the housing, wherein the drive member comprises teeth interacting with the clicker arm in the dose dispensing position of the drive member.

The variation in the friction may result from differing steepness and/or height of the teeth over the axial length of the teeth. As an alternative, the number of clicker arms engaging the teeth may vary corresponding to different relative axial positions of the drive member and the clicker arm. According to a preferred embodiment, the clicker arm is elastically displaceable in a radially outwards direction, with the stiffness of the clicker arm varying over its length in the longitudinal direction. This results in a different resistance required for flexing the clicker arm outwards as it bumps over the clicker arm teeth. For example, due to the higher stiffness of the clicker arm in a proximal part thereof, interaction of the teeth of the drive member with this stiffer part has a higher retarding effect compared with interaction of the teeth of the drive member with a more compliant distal part of the clicker arm. It is preferred if the axial position of the drive member may be amended by actuation of a trigger or dose button. Preferably, the clicker arm may transition from a bending to a torsional deflection regime.

The object of the present invention is further solved by a drug delivery device as defined in claim 4. Such a handheld injection device comprises a dispensing speed control mechanism as defined above and a release button, which is displaceable relative to the housing to initiate dispensing of a set dose, wherein the drive member is coupled to the release button such that axial displacement of the release button is transferred to the drive member.

The injection device may further comprise a dose setting member, which during dose setting rotates relative to the housing in a first direction and which during dose dispensing rotates relative to the housing in a second opposite direction. The dose setting member is preferably the element, which is used to set or amend a dose. The drive member may be rotationally constrained and axially displaceable relative to a piston rod, which is in threaded engagement with the housing. Thus, rotation of the drive member results in an axial displacement of the piston rod on the helical path of the threaded interface with the housing.

According to a preferred embodiment the injection device further comprises a limiting element limiting the rotational movement of the dose setting member between a zero dose position and a maximum dose position. The limiting element may be movable on a first path rotationally constrained but axially displaceable relative to one of the housing or the dose setting member and is movable on a second, helical path relative to the other of the housing or the dose setting member. Preferably, at least one of the first path and the second path has an end stop limiting the relative movement of the limiting element. In other words, a relative rotation of the dose setting member and the housing causes the limiting element to travel on both paths with the movement along the helical path results in a displacement on the axial path or vice versa. Thus, if the movement in one of these paths is stopped by an end stop, further rotation of the dose setting member relative to the housing is prevented. This is used to define a zero dose limit and a maximum dose limit.

By providing an additional element limiting movements in the device at the zero dose position and at the maximum dose position during dose setting and dose dispensing, different designs of the device may be chosen, which e.g. do not require that the dose setting member protrudes from the housing during dose setting. In addition, the force required during dose dispensing may be reduced. The present invention is based on the idea to de-couple a limiting element from a dose setting member such that a relative movement between the dose setting member and the limiting element is allowed. Such a relative movement may be a relative displacement and/or a relative rotation.

According to a preferred embodiment, the limiting element is a nut with an internal thread engaging an external thread on the dose setting member. In this embodiment it is preferred if the limiting element is provided with splines at its radially outer surface which are guided in corresponding splines provided on an inner surface of the housing.

As an alternative, according to a further preferred embodiment, the limiting element is a nut with an external thread engaging an internal thread of the housing. In this embodiment it is preferred if the limiting element is provided with splines at its radially inner surface which are guided in corresponding splines provided on an outer surface of the dose setting member.

The two above embodiments are not limited to the design of the limiting element as a full sleeve or ring-like nut. Moreover, a half nut may be provided extending about 180°. As an alternative to a splined engagement any other suitable means may be provided allowing guiding the limiting element in the housing in a rotationally constrained manner, e.g. a protrusion running in a notch or groove, corresponding teeth, or the like.

To limit movements of the limiter mechanism, a first counter stop is provided at a first end of the limiting element and a second counter stop is provided at an opposite, second end of the limiting element. Preferably the stops are located at the distal and proximal ends of the limiting element, respectively.

According to a further development of this idea, one of the housing or the dose setting member is provided with a first end stop and a second end stop which are located such that the limiter mechanism is in its zero dose position if the first end stop abuts the first counter stop and the limiter mechanism is in its maximum dose position if the second end stop abuts the second counter stop. As an alternative, one of the end stops may be provided on the housing and the other on the dose setting member.

The end stops may simply abut the counter stops in an axial direction during relative movement. However, it is preferred if the first end stop and the first counter stop and/or the second end stop and the second counter stop are rotational stops. Further, end stops and counter stops may be provided by the threaded engagement, i.e. movement is limited by the nut reaching the end of a helical track of a thread.

According to a preferred embodiment, the dose setting member is not axially displaced or wound out of the housing. In other words, the length of the injection device does not change during dose setting and dose dispensing. Preferably, the dose setting member is axially constrained within the housing, e.g. by a snap connection of an annular bead and a corresponding annular notch.

A clutch may be provided interposed between the dose setting member and the drive member, wherein the clutch allows relative rotational movement between the dose setting member and the drive member during dose setting and prevents relative rotational movement between the dose setting member and the drive member during dose dispensing. Thus, as the drive member engages the piston rod, the piston rod will not move during dose setting or dose resetting, but only during dose dispensing.

Preferably, the clutch comprises a clicker mechanism. For example, the dose setting member may be axially constrained within the housing but is free to rotate, resisted by sprung detent features between the dose setting member and the drive member or a component connected to the drive member, e.g. a spool.

These detent features provide positive feedback to the user during dialing.

To provide a visual indication of a set dose, numerals or markings may be provided on a component of the limiter mechanism which are visible from the outside of the housing. According to a preferred embodiment, at least the dose setting member is provided with such numerals or markings. In addition, a further element may be provided with such numerals or markings. In more detail, the dose display may be divided into "tens" and "units", each shown on a separate wheel and which index at different rates. The units may be printed directly onto the dose setting member, e.g. a dial sleeve, and, therefore, index as the dose setting member is rotated. A transfer gear may link the dose setting member and a tens wheel to increment the tens wheel once for every 10 units indexed on the dose setting member. If a clicker is provided in the clutch, the detent features may align the dose setting member with the housing e.g. via a spool and the drive member so the units of the dose display align with the dose window accurately.

To prevent an underdosage or a malfunction, the drug delivery device may comprise a last dose protection mechanism for preventing the setting of a dose, which exceeds the amount of liquid left in a cartridge. For example, the last dose protection mechanism comprises a nut member located interposed between the drive member and the dose setting member or any other component which rotates during dose setting and dose dispensing. In a preferred embodiment, the dose setting member rotates during dose setting and during dose dispensing, whereas the drive member only rotates during dose dispensing together with the dose setting member. Thus, in this embodiment, the nut member will only move during dose setting and will remain stationary with respect to these components during dose dispensing. Preferably, the nut member is threaded to the dose setting member and splined to the drive member. As an alternative, the nut member may be threaded to the drive member and may be splined to the dose setting member. The nut member may be a full nut or a part thereof, e.g. a half nut.

The injection device may comprise a cartridge containing a medicament.

According to a preferred embodiment, the power reservoir for driving the drive member comprises a reverse wound flat spiral spring, which is pre-tensioned to store the energy required to dispense the whole contents of the cartridge. Thus it is not necessary to recharge the spring during use of the device.

The reverse wound flat spiral spring may have a first end attached to a first spool and a second end attached to a second spool, with one of the spools being coupled to the drive member. In other words, the power reservoir may comprise a storage drum and a torque drum arranged close to each other and a strip of spring sheet metal having two ends, each end attached to one of the drums. The strip of spring sheet metal is coiled on the storage drum in a relaxed state. The spring is preferably charged during manufacturing of the device by rotating the torque drum thereby coiling the strip of spring sheet metal onto the torque drum and bending the strip of spring sheet metal the other way round than in the relaxed state thus arriving in a charged state with the strip of spring sheet metal tending to re-coil onto the storage drum thereby generating a torque.

One characteristic of such a spring is that the torque remains relatively constant throughout the transfer of the spring from the torque drum to the storage drum. For this reason the spring mechanism may be called a constant torque motor. This characteristic is particularly suitable for use in dispensing multiple doses of medication because it means that the first (with maximum stored energy in the spring) and last doses (with spring energy almost exhausted) will be delivered with very similar characteristics, such as injection speed and breakout force (this is the force required to overcome the static friction of a bung in the medication cartridge). This means that the spring can be designed around one operating condition, i.e. the torque required to overcome static friction and then to deliver the medication in an appropriate injection time. In a preferred embodiment the strip of spring sheet metal consists of spring steel.

The spring may be attached to one of the spools, preferably the output spool, by boss features on the spool, which engage with holes in the end of the spring such that tension in the spring strip creates torque acting on the spool. The spring is not mechanically anchored to the other spool, i.e. for example the storage spool, since the natural curvature of the spring strip ensures tight coiling around this spool.

As an alternative to the reverse wound flat spiral spring, the power reservoir for driving the drive member may comprise a torsion spring, which is coupled to the dose setting member such that rotation of the dose setting member tensions the spring. This means, that although a preload may be provided in the spring, the user has to strain the spring each time a new dose is set.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-GluTrp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Figure 2:
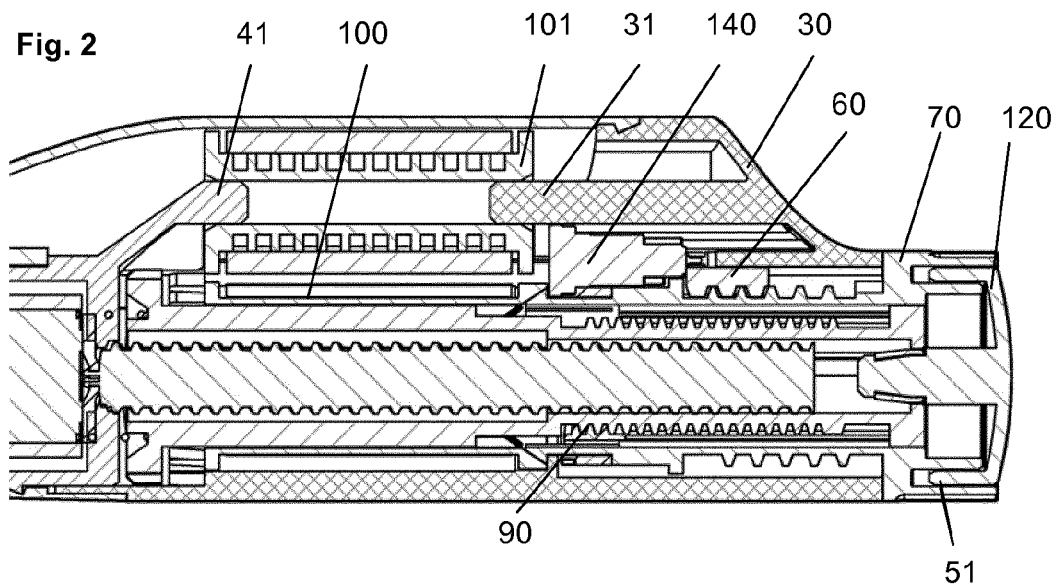
Figure 3:
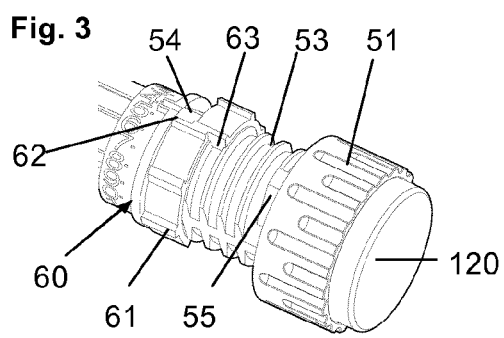
Figure 4:
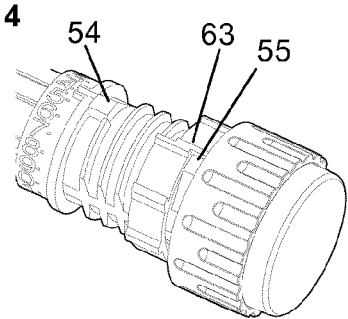
Figure 5:
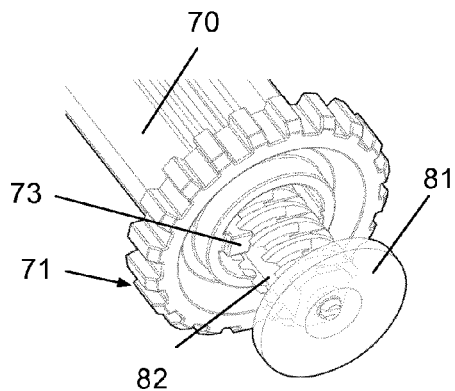
Figure 6:
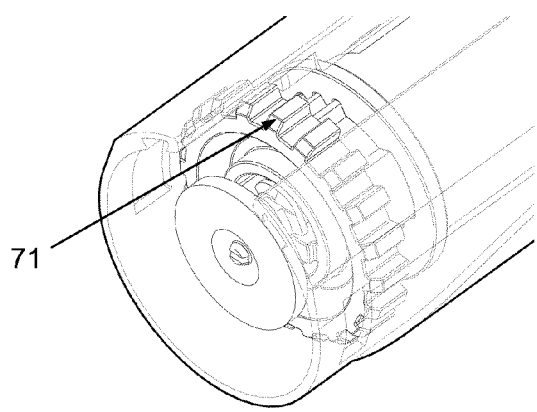
Figure 7:
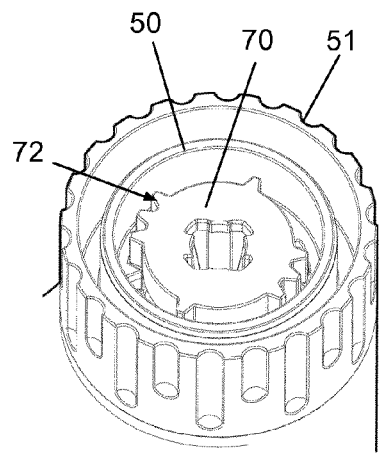
Figure 8:
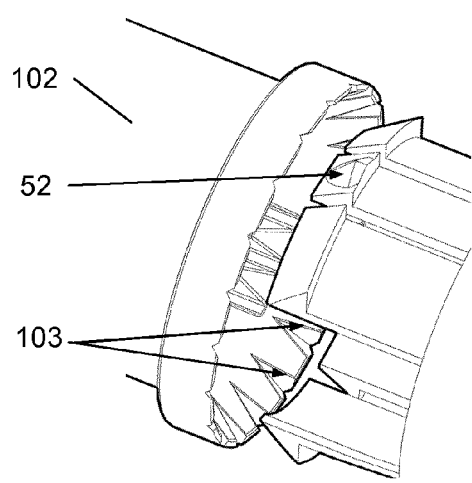
Figure 9:
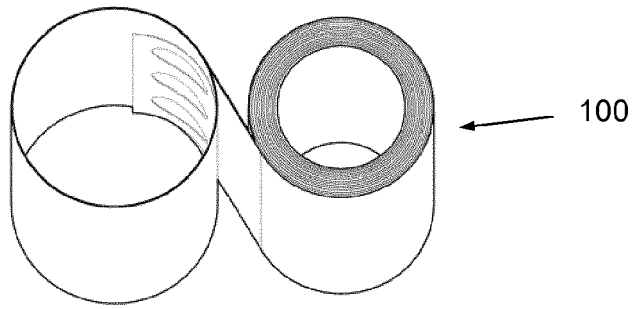
Figure 10A:
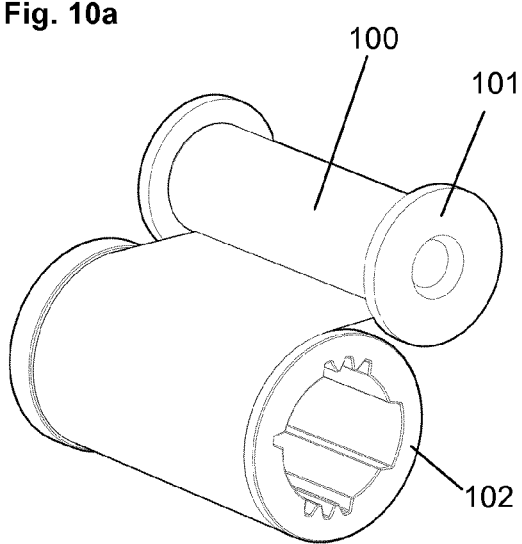
Figure 10B:
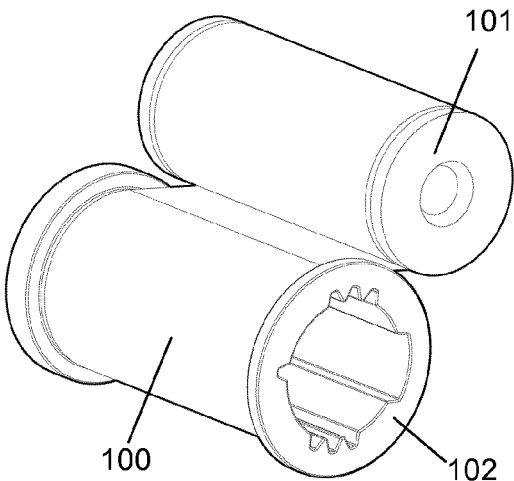
Figure 11:
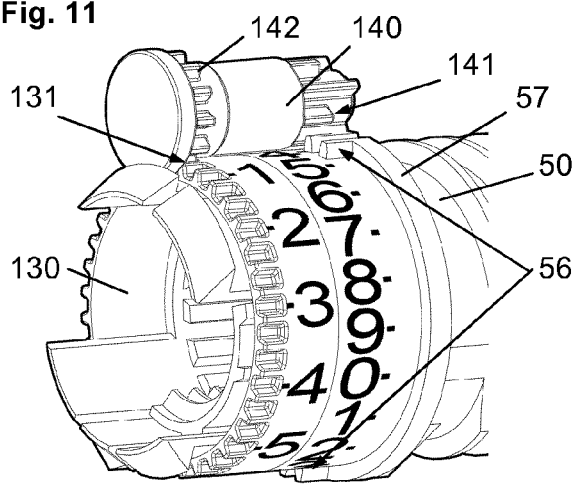
Figure 12:
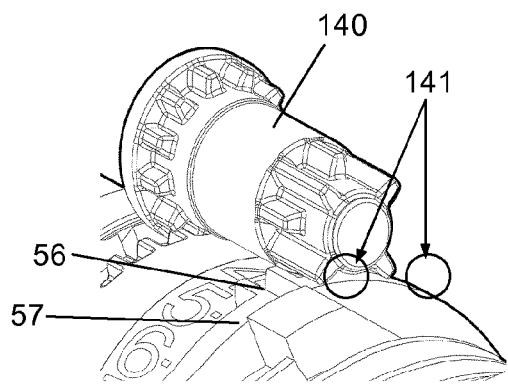
Figure 13:
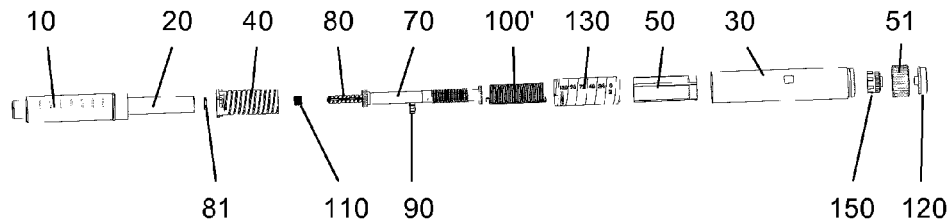
Figure 14:
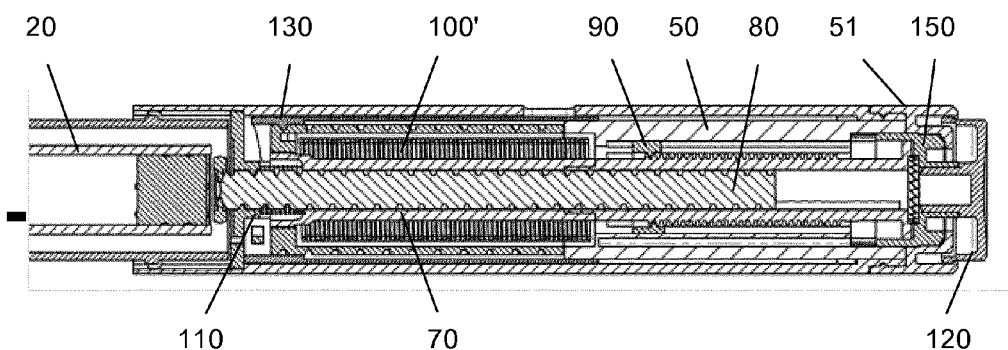
Figure 15:
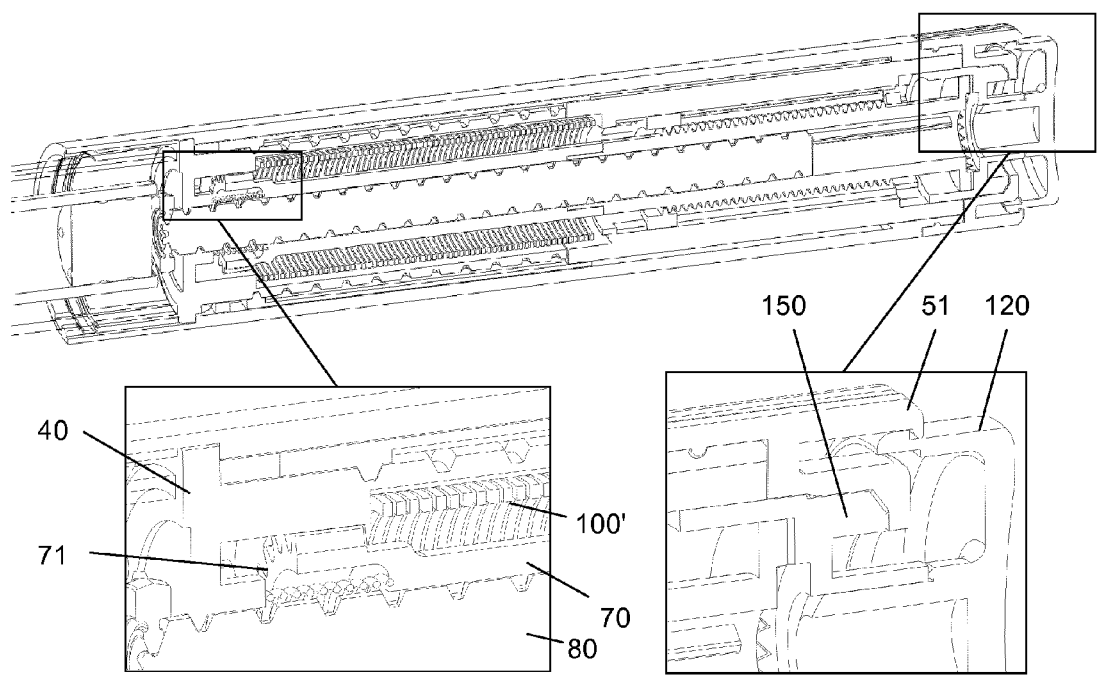
Figure 16:
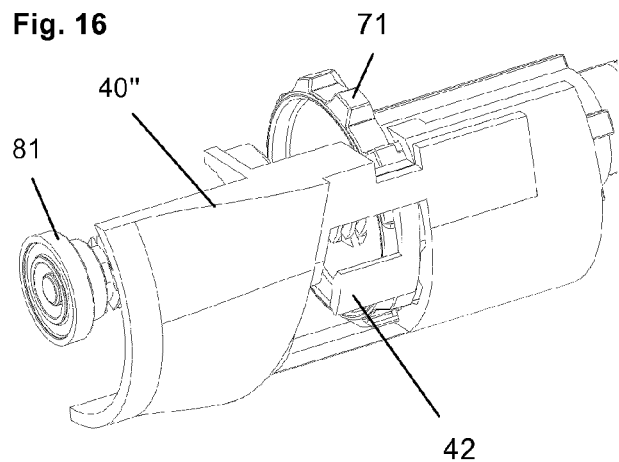
Figure 17A:
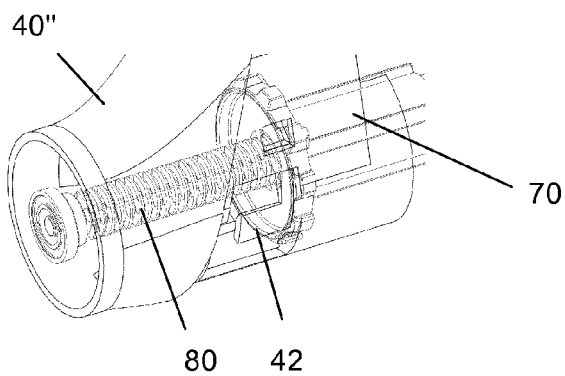
Figure 17B:
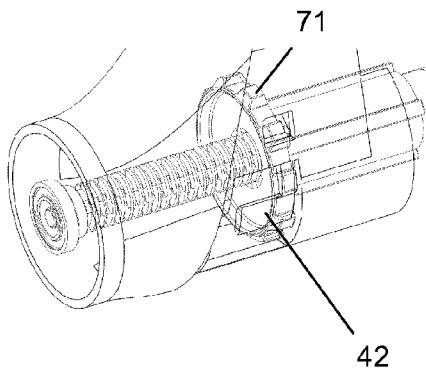
Figure 17C:
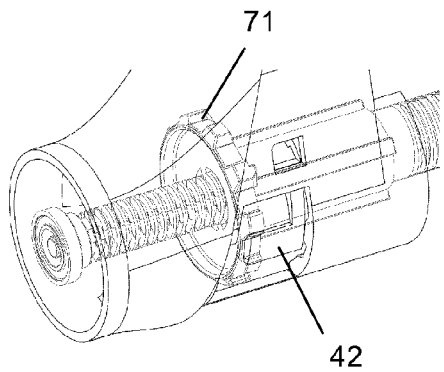
Figure 18A:
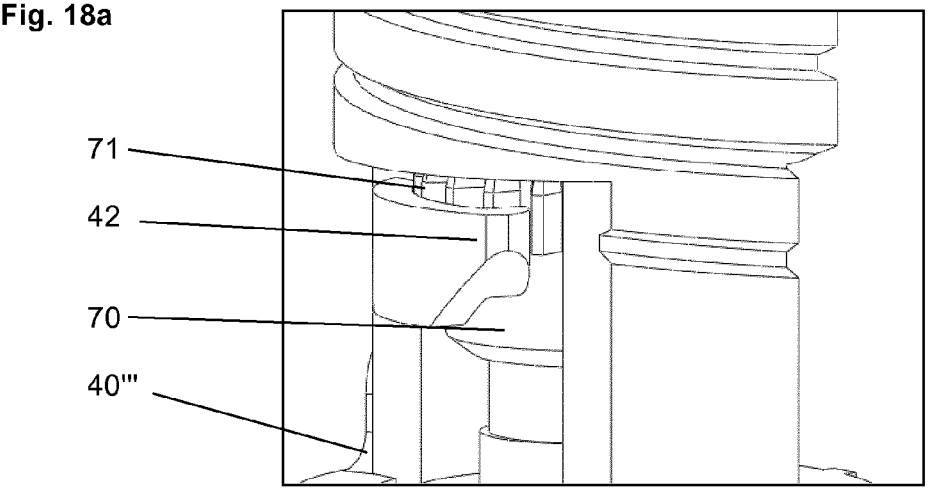
Figure 18B:
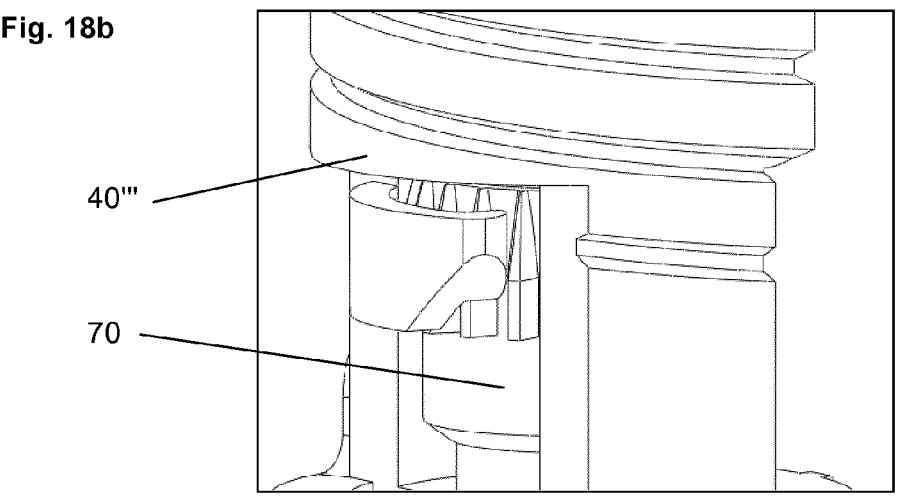
Figure 18C:
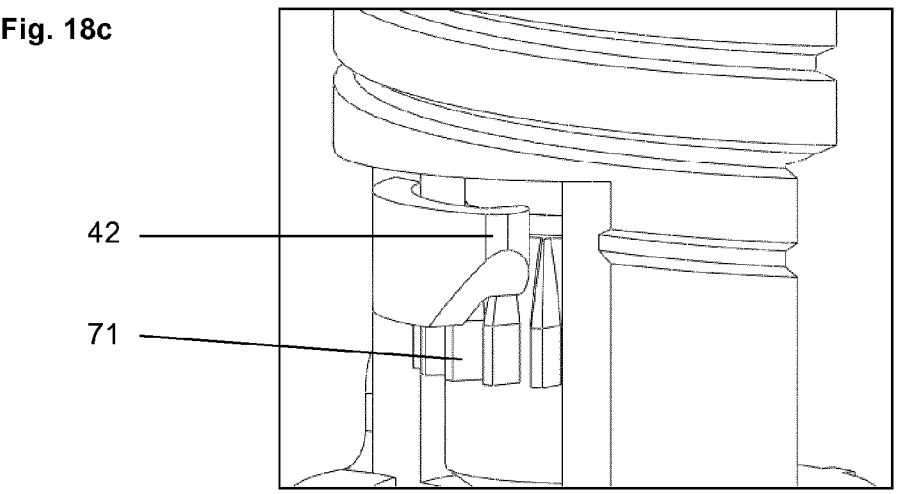

Non-limiting, exemplary embodiments of the invention will now be described with reference to the accompanying drawings, in which:

FIG. 1 shows an exploded view of an injection device comprising a limiter mechanism according to a first embodiment of the invention, FIG. 2 shows a section view of the limiter mechanism of FIG. 1 during dose setting, FIG. 3 shows an enlarged detail of the limiter mechanism of FIG. 1 in the zero dose position, FIG. 4 shows an enlarged detail of the limiter mechanism of FIG. 1 in the maximum dose position, FIG. 5 shows an enlarged detail of the limiter mechanism of FIG. 1, FIG. 6 shows an enlarged detail of the limiter mechanism of FIG. 1, FIG. 7 shows an enlarged detail of the limiter mechanism of FIG. 1, FIG. 8 shows an enlarged detail of the limiter mechanism of FIG. 1, FIG. 9 shows a spring of the limiter mechanism of FIG. 1, FIG. 10a shows the spring of FIG. 9 in its fully charged state, FIG. 10b shows the spring of FIG. 9 in its fully discharged state, FIG. 11 shows an enlarged detail of the limiter mechanism of FIG. 1, FIG. 12 shows an enlarged detail of the limiter mechanism of FIG. 1, FIG. 13 shows an exploded view of an injection device according to a second embodiment of the invention, FIG. 14 shows a section view of the drive mechanism of FIG. 13, FIG. 15 shows a further section view of the drive mechanism of FIG. 13 with two enlarged details, FIG. 16 shows an enlarged detail of an injection device according to a third embodiment of the invention, FIG. 17a shows the detail of FIG. 16 in the dose setting mode, FIG. 17b shows the detail of FIG. 16 in the dose dispensing mode, FIG. 17c shows the detail of FIG. 16 in the dose dispensing mode, and FIGS. 18a-c show a further embodiment of a retarding mechanism in various stages.

An injection device 1 according to the present invention is shown in FIG. 1 in an exploded view, wherein the dispensing speed control mechanism, which is shown in more detail in FIGS. 16 to 17c is not visible in FIGS. 1 to 12. The injection device comprises a cartridge holder 10, a cartridge 20 and a limiter mechanism. The limiter mechanism comprises a housing with an outer housing 30 and an inner housing 40, a dial sleeve as a dose setting member 50 with a dial grip 51, a limiting element 60, a tubular drive member 70, a lead screw 80, a bearing 81, a nut 90, a drive spring 100 with a storage spool 101 and an output spool 102, a return spring 110, a dose button 120, a display wheel 130 and a gear wheel 140. With the exception of the gear wheel 140, the storage spool 101 and the spring 100, all components are located concentrically about a common principle axis of the mechanism. In more detail, the drive member 70 surrounds the lead screw 80, the output spool 102 and the dose setting member 50 surround the drive member 70, and the limiting element 60 and the display wheel 130 surround the dose setting member 50. Further, the nut 90 is located between the drive member 70 and the dose setting member 50.

FIGS. 1 and 2 show cross-sectional views of the limiter mechanism concept incorporated into a pen injector. A medicament cartridge 20 is housed within the cartridge holder 10. The cartridge holder 10 is rigidly constrained in a body defined by the proximal housing part 30 and the distal housing part 40. The cartridge holder 10 provides location and containment of the medicament cartridge 20 and partial protection of the spring 100 and the storage spool 101.

The distal end of the lead screw 80 connects to the bearing 81 to permit relative rotation but prevent axial separation. The distal face of the bearing 81 abuts a bung of the medicament cartridge 20. It is the lead screw 80 and bearing 81 assembly that drives the bung axially in order to deliver medicament. The lead screw 80 has a thread running along its length, which may be a twin-start thread, in addition to splines 82, which may be a plurality of splines.

The distal end of the lead screw 80 is threaded to a thread insert which is formed by the inner housing 40 and the splines 82 in the lead screw 80 engage with axial ribs 73 of the drive member 70 as shown in FIG. 5. Rotation of the drive member 70 thus causes the lead screw 80 to advance axially through the thread insert (moving the bung).

The inner housing 40 with the thread insert is rigidly constrained in the outer housing 30 and provides thread connection to lead screw 80, axial abutment to the trigger spring 110, an axial end stop for the drive member 70, support of the storage spool 101 distal end and location features for the cartridge holder 10.

The trigger spring 110 acts between the inner housing 40 and the drive member 70 and provides a reaction force on the drive member 70 to return it to an "at rest" state which is depicted in FIG. 2.

The drive member 70 provides the mechanical connection between the spring 100 and lead screw 80 to transfer the torque that delivers the drug to the user. In the "at rest" state (0 units dialed, trigger button 120 released) the drive member 70 is splined to the outer housing 30 at the distal end by a ring of teeth 71. Corresponding splines on the outer housing 30 are depicted in FIG. 6. These spline features 71 react the spring 100 torque and prevent uncontrolled release of the spring energy. In other words, a clutch is provided between the outer housing 30 and the drive member 70, which is closed (preventing relative rotation) during dose setting or dose resetting and which is open (allowing relative rotation) during dose dispensing.

The outer surface of the drive member 70 engages with splines on the inner surface of the output spool 102. The drive member 70 and the output spool 102 remain rotationally linked at all times.

In the "triggered" condition (trigger button 120 depressed), the drive member 70 is rotationally coupled to the dose setting member 50 through additional spline features 72 located at the proximal end of the drive member 70 as shown in FIG. 7. Thus, a further clutch is provided between the drive member 70 and the dose setting member 50, which is open (allowing relative rotation) during dose setting or dose resetting and which is closed (preventing relative rotation) during dose dispensing.

The spring 100 is a reverse wound flat spiral spring. FIG. 9 shows an illustrative example of the spring in a partially charged state, with the spools omitted for clarity. In FIGS. 10a and 10b, the spring 100 is wound around two cylindrical spools 101, 102. In the "fully charged" state shown in FIG. 10a (no doses dispensed from cartridge 20) the majority of the spring 100 is back-wound onto the output spool 102 with a small length naturally wound around the storage spool 101. As the spring 100 is discharged (during dose dispense) it winds onto the storage spool 101 and off the output spool 102. The spring 100 remains connected to both the storage spool 101 and output spool 102 at all times. Features on the output spool 102 engage with corresponding features on the end of the spring 100. The spring 100 is not mechanically anchored to the storage spool 101 since the natural curvature of the spring strip ensures tight coiling around the storage spool 101. Once there are a couple of wraps of strip material on the output spool, the force at the achorage is negligible. The torque is generated by a more complex combination of the strip un-bending from its backwound state as it leaves the output spool and further un-bending of the strip as assumes its natural formed diameter as it winds itself onto the storage spool.

The storage spool 101 is positioned off axis to the lead screw 80 by a location boss 41 of the inner housing 40 at the distal end and a location boss 31 of the outer housing 30 at the proximal end. The location bosses 31, 41 permit free rotation of the storage spool 101 whilst constraining axial translation.

The trigger button 120 is axially, but not rotationally, constrained within the proximal end of the drive member 70. User input force applied in the distal direction to the trigger button 120 is reacted through the drive member 70 by the trigger spring 110. The end stop for this user input is provided by the inner housing 40 acting on the distal end of the drive member 70. On release of the trigger button 120 the trigger spring 110 returns the drive member 70 in the proximal direction to the "at rest" position (FIG. 2).

The dose setting member 50 is positioned towards the proximal end of the device allowing setting and cancelling (resetting) of a dose by rotation of the grip features 51 on it that can be accessed by the user. The dose setting member 50 is axially constrained within the outer housing 30 but is free to rotate, resisted by sprung detent features 52, 103 between the dose setting member 50 and output spool 102 (see FIG. 8). These detent features 52, 103 provide positive feedback to the user during dialing and align the dose setting member 50 with the outer housing 30 via the output spool 102 and drive member 70 so the units of the dose display which is provided on the dose setting member 50 align with a dose window of the outer housing 30 accurately.

The limiting element 60 is a dose nut with an internal thread which engages a threaded section 53 on the dose setting member 50 and external splines 61 meshing splines of the outer housing 30. The limiting element 60 is thus rotationally constrained to the outer housing 30 but axially displaceable relative to the outer housing 30. In the embodiment of FIGS. 1 to 12, the limiting element 60 has the form of a half nut. However, the limiting element 60 may also be provided as a full nut. Rotation of the drive member 70 by the spring 100 is metered by the limiting element 60 via the dose setting member 50. The limiting element 60 provides the zero unit stop in its most distal position (FIG. 3) and maximum dose unit stop when in its most proximal position (FIG. 4). However, as an alternative, the limiting element 60 may run in the opposite direction. Abutments 54, 55 on the dose setting member 50 engage corresponding abutments 62, 63 on the limiting element 60 to create positive stop positions.

Because the outer surface of the limiting element 60 is splined to the housing 30 and the inner surface of the limiting element 60 is threaded to the dose setting member 50, a clockwise (CW) rotation of the dose setting member 50 translates the limiting element 60 in the proximal direction. Since the limiting element 60 provides the end of dose stop, the features 54, 62 and 55, 63 interacting at this point are designed to be particularly robust to minimize the risk of failure.

The dose display mechanism shows the dose set that has been set by the user and also the dose remaining as a dose is dispensed. Three components interact to provide numerical display through a transparent window 32 component secured within the outer housing 30.

The dose display is divided into "tens" and "units", each shown on a separate wheel and which index at different rates. The units are printed directly onto the dose setting member 50 and, therefore, index as the dose setting member 50 is rotated. The gear wheel 140 acts as a transfer gear which links the dose setting member 50, i.e. the units, and the display wheel 130 which is the tens wheel to increment the display wheel 130 once for every 10 units indexed on the dose setting member 50.

The dose setting member 50 incorporates two pairs of gear teeth 56 at diametrically opposing positions (see FIG. 11). These teeth 56 engage the smaller pitch circle diameter (PCD) gear teeth 141 of the gear wheel 140 and create intermittent rotation of the gear wheel 140 twice per dose setting member 50 revolution. The display wheel 130 incorporates gear teeth 131 around the entire circumference which are always meshed with the larger PCD gear teeth 142 of the gear wheel 140.

The dose setting member 50 has 20 numbers printed around its circumference (0, 1, 2 . . . 8, 9, 0, 1, 2 . . . 8, 9). The positions of the gear teeth 56 correspond to the index of the display wheel 130 (tens) in relation to the rotation of the dose setting member 50. As the units display indexes from "9" to "0" the teeth 56 on the dose setting member 50 engage with the gear wheel 140 and create a one quarter turn of the transfer gear wheel 140. This rotation delivers a one-twelfth rotation of the tens display wheel 130 corresponding to the pitch of the printed numbers.

Free rotation of the transfer gear wheel 140 is prevented by removing half the length of the gear teeth 141 at alternate positions at the extreme proximal end of the gear wheel 140 (see FIG. 12). This modified gear profile interferes with a circumferential rib 57 on the dose setting member 50, fixing rotation of the gear wheel 140 when not in positive engagement with the dose setting member 50 gear teeth. Two reliefs in this rib 57 permit rotation of the gear wheel 140 corresponding to engagement of the dose setting member 50 gear teeth.

In this embodiment the maximum dose display possible is 129 although the mechanism may be limited to a lower maximum number of units, e.g. 80 units, by the limiting element 60. Altered gear ratios and frequency of tens display wheel 130 index provide options for alternative dose displays. In order to improve robustness of the gear engagement an alternative embodiment of the display mechanism modifies the modulus of the gear teeth. Replacing the pair of teeth 56 on the dose setting member 50 with a single tooth permits the use of larger gear teeth with greater height of engagement. The single relief in the dose setting member 50 circumferential rib (that prevents rotation of the tens display wheel 130 when not indexing) is replaced with a pair of reliefs either side of the single tooth.

In the following, operation of the limiter mechanism is explained in more detail: For dose setting, the dose setting member 50 is rotated by the user in a CW direction to set a dose. The dose can be cancelled by rotating the dose setting member 50 in a counter clockwise (CCW) direction either before any dispense or, alternatively, if the trigger button 120 is released mid-dispense, the remaining dose may be cancelled. The selected dose is displayed through the window 32 in the housing 30 via the dose display mechanism described previously. Irrespective of whether the dose setting member 50 is rotated CW or CCW the dose displayed will always indicate the dose to be dispensed. In addition, the dose display also decrements as the dose is dispensed and thus displays the dose remaining to be dispensed.

As the dose is dialed up the limiting element 60 is driven in the proximal direction along the threaded connection with the dose setting member 50. The dose setting member 50 can be rotated by the user in both CW and CCW directions when the limiting element 60 is not in contact with the zero dose or maximum dose stop abutments 54, 55 of the dose setting member 50. The end of dose abutment 54, 62 prevents CCW rotation of the dose setting member 50 below the 0 unit position. The maximum dose abutment 55, 63 prevents setting of a dose greater than the mechanism maximum, e.g. 80 units.

The detent feature 52, 103 between dose setting member 50 and output spool 102 controls the position of the dose setting member 50 to ensure that discrete units are selected and that the spline features between drive member 70 and dose setting member 50 are correctly aligned to permit spline meshing when the device is triggered.

During dose setting the drive member 70 is coupled to the outer housing 30 via splines (teeth 71) at its distal end and biased into engagement with these splines by the trigger spring 110. The drive member 70 is, therefore, fixed rotationally during dose set which, in turn prevents rotation of the output spool 102 and lead screw 80.

The mechanism incorporates a last dose nut 90 to prevent setting a dose greater than that which remains within the medicament cartridge. This is positioned between the dose setting member 50 and drive member 70 since the dose setting member 50 rotates relative to the drive member 70 during dose set and not during dispense. The nut 90 is splined to the inner surface of the dose setting member 50 and threaded to the drive member 70 such that CW rotation of the dose setting member 50 rotates the last dose nut 90 and translates it in the distal direction. As an alternative, the last dose nut 90 may be splined to the drive member 70 and threaded to the dose setting member 50. The last dose nut 90 is successively translated distally as doses are set and dispensed until the cartridge dose limit is reached. At this point the nut 90 contacts an abutment on the drive member 70 which prevents further CW rotation of the last dose nut 90 and, therefore, CW rotation of the dose setting member 50. The number of permissible rotations of the last dose nut 90 is determined by the capacity of the cartridge 20.

The device may be triggered by the user through application of an axial force on the trigger button 120 in the distal direction. The trigger button 120 acts on the drive member 70, translating the drive member 70 and last dose nut 90 in the distal direction, compressing the trigger spring 110. As the drive member 70 translates it first engages with the dose setting member 50 through splines 72 towards the proximal end of the device. At this stage (trigger button 120 mid position) the dose setting member 50 can no longer be rotated in either direction since the splines 71 at the distal end of the drive member 70 remain in engagement with the outer housing 30. This distal translation of the drive member 70 also engages a dispense feedback clicker feature (not shown in FIGS. 1 to 12, but in FIGS. 16 to 17c) of the outer housing 30 with the distal drive member 70 splines 71. Further distal translation of the trigger button 120 decouples the distal drive member 70 splines 71 from the outer housing 30, releasing rotation of the drive member 70 and spring 100 assembly.

On triggering, the torque generated by the spring 100 turns the drive member 70 and lead screw 80 via the output spool 102. Since the drive member 70 and dose setting member 50 are rotationally connected the dose setting member 50 also rotates during dispense in a CCW direction, translating the limiting element 60 distally. At the zero unit position the limiting element 60 contacts the abutment 54 on the thread to the dose setting member 50, preventing further rotation of the dose setting member 50, drive member 70, lead screw 80 and output spool, ending the dose dispense (FIG. 3).

The trigger button 120 is subsequently released, re-engaging the spline features 71 between drive member 70 and housing 30 thus locking rotation of the drive member 70, lead screw 80 and output spool 102 independent of the limiting element 60 to dose setting member 50 stop feature. This allows the next dose to be set without immediate release of the spring 100. Aside from the lead screw 80 assembly, spring 100 assembly and nut 90 all other components in the device return to their original positions once the entire dose has completed dispense. In reality, the orientation of the drive member, dial grip and trigger button may be different than their original positions, but this may be overlooked as the components have rotational symmetry.

The spline teeth in the housing 30 that engage with the drive member 70 are angled so the drive member 70 is turned against the spring torque as they re-engage when the trigger button 120 is released. Back-winding the drive member 70 retracts the lead screw 80 assembly and ensures that the drive member 70 to housing 30 splines act as the end of dose stop in place of the limiting element 60. The back-winding of the drive member 70 removes the effect of clearances within the mechanism (as a result of designing for manufacturing tolerances or assembly) which could otherwise lead to slight advancement of the lead screw 80 and medicament dispense when the device is dialed for the subsequent dose.

The limiter mechanism provides a platform for the development of a range of pen injectors that provide delivery of a user variable medicament dose with relatively very low user setting torque and user injection force. There is potential for the variable dose to have any predefined maximum dose with resolution to the nearest 0.01 ml (or larger).

A second embodiment of a drug delivery device is shown in FIGS. 13 to 15, however again with the dispensing speed control mechanism, which is shown in more detail in FIGS. 16 to 17c, not visible.

The injection device comprises a cartridge holder 10, a cartridge 20 and a drive mechanism. The drive mechanism comprises an outer housing 30, an inner housing 40, a dose dial sleeve as a dose setting member 50, a number sleeve as a display member 130, a drive sleeve as a drive member 70, a piston rod 80, a bearing 81, a nut 90, a drive spring 100', a return spring 110, a dial grip 51, a dose button 120 and a clutch plate 150. All components are located concentrically about a common principle axis of the mechanism. In more detail, the drive member 70 surrounds the piston rod 80, the torsion spring 100' surrounds the drive member 70, the dose setting member 50 and the inner housing 40 surround the torsion spring 100', the display member 130 surrounds the dose setting member 50 and the outer housing 30 surrounds the display member 130. Further, the nut 90 and the clutch plate 150 are located between the drive member 70 and the dose setting member 50.

The dose button 120 is axially constrained to the clutch plate 150. As can be seen in FIG. 14, this may be achieved by a snap-on connection with the clutch plate 150 having an opening for receiving a pin of the dose button 120. Thus, the dose button 120 may be rotatable with respect to the clutch plate 150.

The dial grip 51 is axially constrained to the outer housing 30 which forms a body for the drive mechanism. Again, as shown in FIG. 15, this may be achieved by a snap-on connection between the dial grip 51 and the outer housing 30. The dial grip 51 is rotationally constrained to the clutch plate 150. In the embodiment of FIGS. 13 to 15 a splined interface is provided between the dial grip 51 and the clutch plate 150. This splined interface is disconnected when the dose button 120 is pressed, i.e. when the dose button 120 and the clutch plate 150 are moved axially relative to the dial grip 51 and the outer housing 30.

The clutch plate 150 is further rotationally constrained to the dose setting member 50. Again, a splined interface may be provided between the clutch plate 150 and the dose setting member 50. The clutch plate 150 is further coupled to the drive member 70 via a ratchet interface which occurs on axial abutment. The ratchet interface provides a detented position between the dose setting member 50 and the drive member 70 corresponding to each dose unit and engages different ramped tooth angles during clockwise and anti-clockwise relative rotation between the dose setting member 50 and the drive member 70. This ratchet interface forms a clutch with corresponding teeth provided on the clutch plate 150 and the drive member 70, respectively.

The display member 130 is rotationally constrained to the dose setting member 50. Again, a splined interface may be provided between the display member 130 and the dose setting member 50. The display member 130 is further constrained to move along a helical path relative to the inner housing 40. This may be achieved by a threaded interface between the display member 130 and the inner housing 40. As an alternative, a threaded interface may be provided between display member 130 and the outer housing 30. The display member 130 is marked with a sequence of numbers which are visible through a window in the outer housing 30. As an alternative to a transparent window an aperture could be provided in the outer housing 30. The window allows the user to denote the dialed dose of medicament. The window may be or may comprise a magnifying lens. The window may be an integral part of the outer housing 30 or a separate component attached to the housing.

The nut 90 acts as a last dose nut and is interposed between the dose setting member 50 and the drive member 70. The nut 90 is rotationally constrained to the dose setting member 50, e.g. via a splined interface. Thus, the nut 90 may be axially displaced relative to the dose setting member 50. The nut 90 moves along a helical path relative to the drive member 70, e.g. via a threaded interface, when relative rotation occurs between the dose setting member 50 and the drive member 70, i.e. during dose setting and dose resetting. An end stop (not shown) may be provided to limit the movement of the nut 90 in the track defined by the threaded interface. As an alternative, the nut may be splined to the drive member 70 and threadedly engaged with the dose setting member 50.

The drive member 70 extends from the interface from the dose setting member 50 down to a splined tooth interface (teeth 71) with the inner housing 40, which provides a clutch between the inner housing 40 and the drive member 70. This provides rotational constraint of the drive member 70 to the inner housing 40 during dialing. When the dose button 120 is pressed, the drive member 70 is distally displaced causing the splined teeth 71 of the clutch to disengage, so that rotation of the drive member 70 relative to the inner housing 40 is allowed. This axial displacement of the drive member 70 causes engagement of the drive member 70 with a ratchet feature which provides an audible and/or tactile feedback during dose dispensing. The ratchet feature may comprise an inwardly directed compliant clicker finger bumping over the splined teeth 71 which are disengaged from the housing.

The inner housing 40 is rigidly fixed to the outer housing 30. Thus, neither any rotation nor any axial movement between the inner housing 40 and the outer housing 30 is possible. The inner housing 40 and the outer housing 30 may be formed as one integral part, however due to manufacturing reasons it is preferred to provide the housing as the two separate components of the outer housing 30 and the inner housing 40.

The drive spring 100' is a torsion spring which is attached at one end to the inner housing 40 and at the other end to the dose setting member 50. The drive spring 100' is pre-wound upon assembly, such that it applies a torque to the dose setting member 50 when the mechanism is at zero units dialed. The action of rotating the dial grip 51 to set a dose rotates the dose setting member 50 relative to the inner housing 40 and winds up the drive spring 100'. The drive spring 100' has the function of driving the drive member 70 during dispensing. In more detail, the drive spring 100', via the dose setting member 50, provides the torque which rotates the drive member 70 which in turn advances the lead screw 80.

The piston rod 80 is rotationally constrained to the drive member 70 e.g. via a splined interface. When rotated, the piston rod 80 is forced to move axially relative to the drive member 70. This is achieved by a threaded interface between the piston rod 80 and the inner housing 40. The bearing 81 is axially constrained to the piston rod 80 and acts on the bung within the cartridge 20 during dose dispensing.

The axial position of the drive member 70, the clutch plate 150 and the dose button 120 is defined by the action of the return spring 110 which abuts the inner housing 40 and applies a force on the drive member 70 in the proximal direction. This ensures that the clutch plate 150 is in splined engagement with the dial grip 51 and that the drive member 70 is in splined engagement with the inner housing 40. The return spring 110 also acts to maintain the engagement of the ratchet features between the drive member 70 and the clutch plate 150, i.e. to maintain the engagement of the clutch.

The outer housing 30 provides location for the cartridge 20 and the cartridge holder 10 which can be attached to the outer housing 30. Further, the outer housing 30 comprises an interface to rigidly constrain the inner housing 40 and a groove on its external surface to axially retain the dial grip 51. Further, a removable cap may be provided which fits over the cartridge holder 10 and is retained via clip features.

A dispense clicker, which may also serve as a speed control mechanism, is described with respect to FIGS. 16 to 17c. This dispense clicker may be incorporated in any of the devices as described above, in which the drive member 70 is moved axially during dispense. This releases its splined engagement 71 with the housing (distal or inner housing 40, 40'), allowing it to be rotated by the stored energy source (spring 100). The rotation of the drive member 70 causes the lead screw 80 to advance through a thread and dispense medicament.

The mechanism described here contains a radially-acting dispense clicker arm 42 formed within the housing that acts on teeth 71 on the drive member 70, which changes in stiffness as the drive member 70 moves in an axial direction. The stiffness of this clicker arm 42 determines the frictional drag on the drive member 70 and hence the speed at which the device dispenses the medicament, as the torque which drives drive member 70 is approximately constant regardless of the dialed dose or the remaining medicament in the cartridge 20. However, in the second embodiment the spring is charged during dose setting (dialing).

The stiffness is highest (as embodied) when the dose button 120 is displaced by the smallest displacement necessary to release the spline features 71 allowing the drive member 70 to rotate and dispense the medicament. As the dose button 120 (and hence the drive member 70) is displaced further towards the mechanism body, the clicker stiffness is reduced so that the frictional drag torque decreases, allowing the drive member 70 to rotate at a higher speed.

The spline features (teeth 71) on the drive member 70 have two functions. They primarily lock the drive member 70 to the housing, when the pen is in dose select (dialing) mode (see FIG. 17*a*). They also act as ratchet features over which the clicker arm 42 passes and detents into discrete single unit positions (FIGS. 17*b* and 17*c*). The profile of these teeth 71 in conjunction with the tip profile and cantilever characteristics of the ratchet arm 42 determines the drag torque applied by the dispense clicker.

The cantilevered clicker arm 42 is designed to work either primarily in bending or primarily in torsion, depending on the axial position of the drive member 70. Then the dose button 120 is pressed just enough to leave the dialing mode and enter dispense mode (drive member 70 clutch teeth 71 to thread insert are disengaged, see FIG. 17*b*), the clicker arm 42 is in a pure bending regime. As the dose button 120 is pressed progressively further (see FIG. 17*c*), the clicker arm 42 becomes more torsionally loaded. The L-shaped geometry of the cantilever means that the effective cantilever stiffness is significantly less in torsion compared with pure bending, therefore the clicker drag torque becomes less. The less-stiff clicker arm torque requires less energy for the clutch teeth 71 to overcome, so the resultant speed of dispense becomes greater as less energy is required to overcome the clicker mechanism and more of the stored energy is converted to driving the lead screw 80 forward, dispensing medicament.

The range of clicker torques available to limit dispense speed is continuous, but limited by the stroke of the drive member 70 which may be determined by clutch teeth 71 engagement required for robustness and for ergonomic considerations. The degree to which the clicker arm 42 retards speed of dispense can be tuned so that an acceptable range of speeds can be produced. The simple change in cantilever regimes allows a large range of clicker stiffnesses to be designed with a relatively short axial travel of the drive member 70, and so this feature can be applied to a range of mechanisms where a stored energy source is used.

An alternative embodiment (not shown) would have an increasing clicker torque as the dose button 120 is pressed by an increasing amount towards the mechanism body. This would produce slower dispense speed as the dose button 120 is pressed displaced further towards the mechanism body.

Generally, there are two main embodiments for the injection speed control mechanism in that the injection speed retards (decelerates) either if a user presses the trigger element and/or if a user releases the trigger element, e.g. depressing the trigger means such that the injection speed tends to zero.

A further embodiment of a retarding mechanism is shown in FIGS. 18*a* to 18*c*. Similar to FIGS. 17*a* to 17*c*, only a distal portion of an injection device is shown. However, this retarding mechanism may be implemented in various injection devices at any suitable position. In this further embodiment, during dose setting and dose cancelling the drive sleeve 70 is splined to a housing component, for example an inner body 40''', via corresponding spline teeth. In this embodiment, the drive sleeve splines 71 are elongated and also tapered. Initially, the splines 71 are in full engagement with the inner body 40''' and therefore the drive sleeve 70 is locked against rotation.

After sufficient dose button travel to disconnect the drive sleeve splines 71 from the inner body 40''', the clicker arm 42 is in maximum engagement with the drive sleeve splines 71. This creates a maximum drag torque on the drive sleeve 70 slowing the dispense speed. Further dose button travel moves the drive sleeve 70 axially which progressively decreases the depth of engagement of the splines 71 with the clicker 42. As the engagement decreases, the drag torque applied by the clicker 42 to the drive sleeve 70 decreases and therefore the dispense speed increases. Thus, by increasing the travel of the dose button, proportional speed control can also be added to the mechanism. In this instance, initial travel of the dose button unlocks the drive sleeve 70 from the inner body 40''', and further travel increases the speed of dispense. The same principle of the retarding mechanism applies to a not shown embodiment, where instead of a housing or body part, any other component, which is rotationally constrained to the housing, carries the clicker which engages the drive sleeve splines.

The invention claimed is:

1. A dispensing speed control mechanism for use in an injection device, the mechanism comprising:
   a housing;
   a drive member;
   a power reservoir to drive the drive member, the power reservoir axially movable between a dose setting position in which the drive member is rotationally constrained to the housing, and a dose dispensing position in which the drive member is rotationally de-coupled from the housing; and
   a friction member configured to retard the drive member during dose dispensing depending on the axial position of the drive member.

2. The mechanism according to claim 1, wherein the friction member comprises a clicker mechanism comprising a clicker arm rotationally constrained to the housing, wherein the drive member comprises teeth interacting with the clicker arm in the dose dispensing position of the drive member.

3. The mechanism according to claim 2, wherein the clicker arm is elastically displaceable in a radially outwards direction, wherein a stiffness of the clicker arm varies over a length of the clicker arm in the longitudinal direction.

4. A handheld injection device comprising:
   a dispensing speed control mechanism comprising:
      a housing;
      a drive member;
      a power reservoir to drive the drive member, the power reservoir axially movable between a dose setting position in which the drive member is rotationally constrained to the housing, and a dose dispensing position in which the drive member is rotationally de-coupled from the housing; and a friction member configured to retard the drive member during dose dispensing depending on the axial position of the drive member; and a release button displaceable to initiate dispensing of a set dose, wherein the drive member is coupled to the release button such that axial displacement of the release button is transferred to the drive member.

5. The injection device according to claim 4, further comprising a dose setting member, wherein, during dose setting, the dose setting member rotates relative to the housing in a first direction, and wherein, during dose dispensing, the dose setting member rotates relative to the housing in a second opposite direction.

6. The injection device according to claim 5, further comprising a limiter mechanism with a limiting element configured to limit the rotational movement of the dose setting member between a minimum dose position and a maximum dose position, wherein the limiting element is movable on a first path rotationally constrained and axially displaceable relative to at least one of the housing or the dose setting member, and is movable on a second, helical path relative to the other of the housing or the dose setting member, and wherein at least one of one of the first path and the second path has an end stop limiting the relative movement of the limiting element.

7. The injection device according to claim 5, wherein the dose setting member is axially constrained within the housing.

8. The injection device according to claim 5, further comprising a clutch provided interposed between the dose setting member and the drive member, wherein the clutch allows relative rotational movement between the dose setting member and the drive member during dose setting and prevents relative rotational movement between the dose setting member and the drive member during dose dispensing.

9. The injection device according to claim 4, further comprising a piston rod, wherein the drive member is rotationally constrained and axially displaceable to the piston rod, and wherein the piston rod is in threaded engagement with the housing.

10. The injection device according to claim 4, wherein at least the dose setting member is provided with markings visible from the outside of the housing.

11. The injection device according to claim 10, further comprising a display wheel comprising markings visible from the outside of the housing, the display wheel coupled to the dose setting member by a gear wheel (140), wherein rotation of the gear wheel (140) causes intermitted rotation of the display wheel (130).

12. The injection device according to claim 10, further comprising a last dose protection mechanism configured to prevent the setting of a dose which exceeds the amount of liquid left in a cartridge and a limiter interposed between the drive member and the dose setting member.

13. The injection device according to claim 4 comprising a cartridge containing a medicament.

14. The injection device according to claim 13, wherein the power reservoir comprises a reverse wound flat spiral spring pre-tensioned to store energy required to dispense contents of the cartridge.

15. The injection device according to claim 13, wherein the power reservoir comprises a torsion spring coupled to the dose setting member such that rotation of the dose setting member tensions the spring.

* * * * *